United States Patent [19]
Johansen

[11] Patent Number: 6,053,882
[45] Date of Patent: Apr. 25, 2000

[54] CAST VENTILATION SLEEVE

[76] Inventor: Jan S. Johansen, 21015 SE. 14th Pl., Issaquah, Wash. 98027

[21] Appl. No.: 08/700,735

[22] Filed: Aug. 15, 1996

[51] Int. Cl.⁷ ........................................................ A61F 5/00
[52] U.S. Cl. .................................................. 602/14; 602/3
[58] Field of Search ........................ 128/DIG. 20; 602/3, 602/9, 13, 14, 6; 601/11, 15, 16, 17, 148

[56]         References Cited

U.S. PATENT DOCUMENTS

| | | |
|---|---|---|
| 726,791 | 4/1903 | Armbruster . |
| 1,652,954 | 12/1927 | Pierce . |
| 2,273,792 | 2/1942 | Brown . |
| 2,837,088 | 6/1958 | Moses . |
| 3,116,731 | 1/1964 | Baxter . |
| 3,307,537 | 3/1967 | Simon et al. ................ 602/14 X |
| 3,314,419 | 4/1967 | Quick ........................ 602/14 X |
| 3,477,427 | 11/1969 | Lapidus . |
| 3,653,083 | 4/1972 | Lapidus . |
| 3,908,642 | 9/1975 | Vinmont . |
| 3,998,220 | 12/1976 | Cleer, Jr. et al. . |
| 4,269,175 | 5/1981 | Dillon . |
| 4,308,862 | 1/1982 | Kalmar . |
| 4,387,710 | 6/1983 | Beatty, III . |
| 4,898,160 | 2/1990 | Brownlee . |
| 5,447,504 | 9/1995 | Baker et al. ................ 602/14 X |

Primary Examiner—Richard J. Apley
Assistant Examiner—Denise Pothier
Attorney, Agent, or Firm—Bruce A. Kaser

[57]                ABSTRACT

The invention is a ventilation sleeve for reducing skin irritation and odor associated with broken limbs which are immobilized for significant periods of time by casts or the like. The ventilation sleeve is an elongated flexible bag which is positioned between the cast and skin. One side of the bag has a plurality of ventilation openings through which pressurized air aerates the cast.

1 Claim, 4 Drawing Sheets

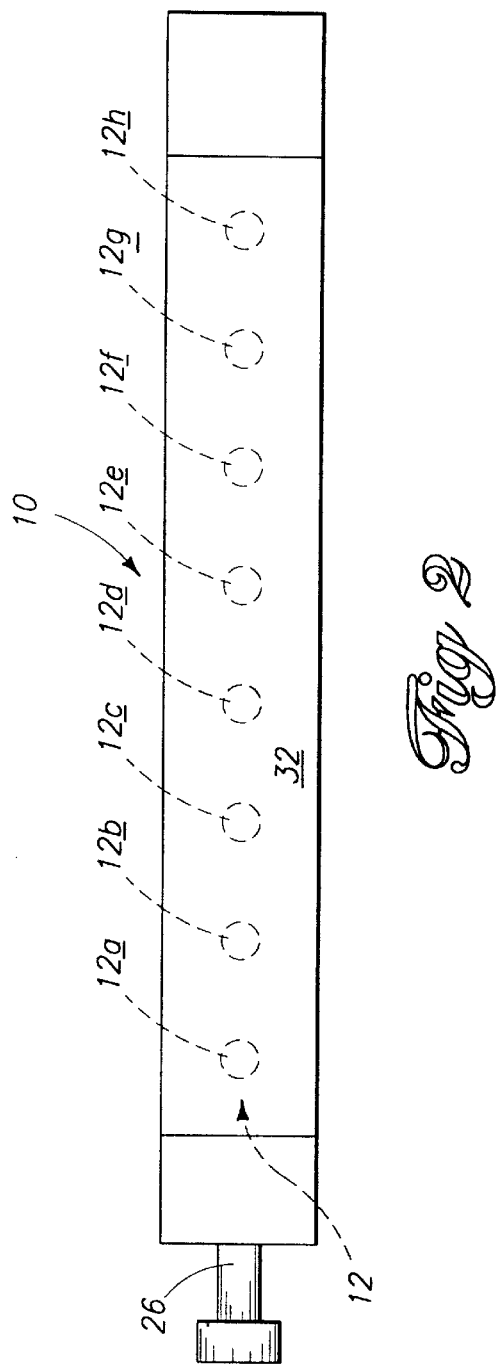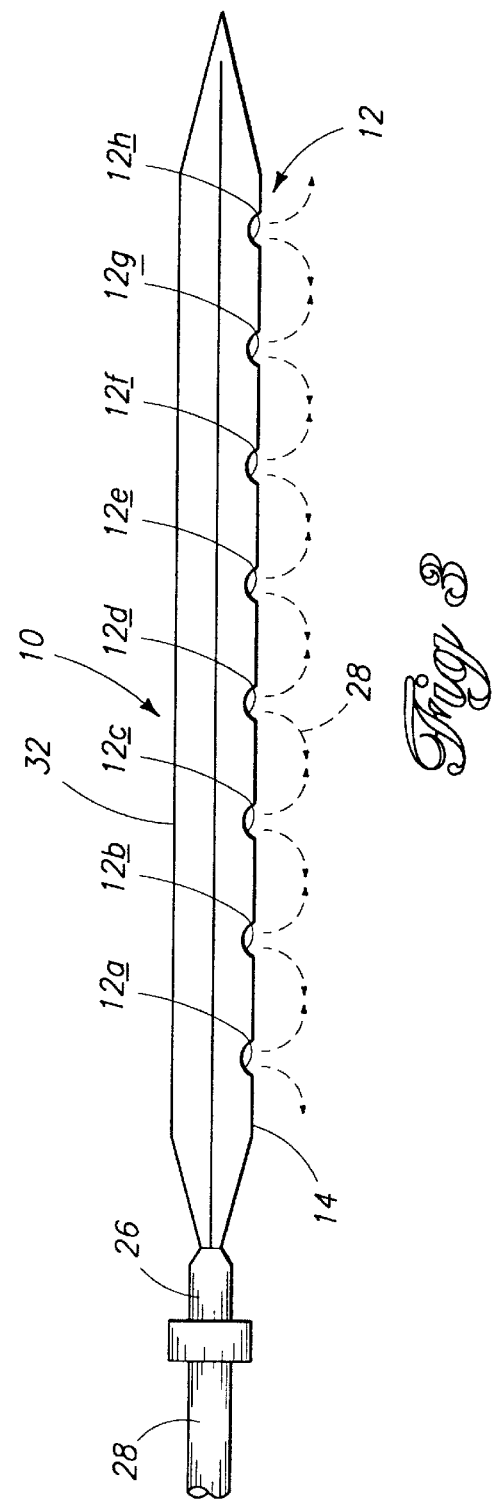

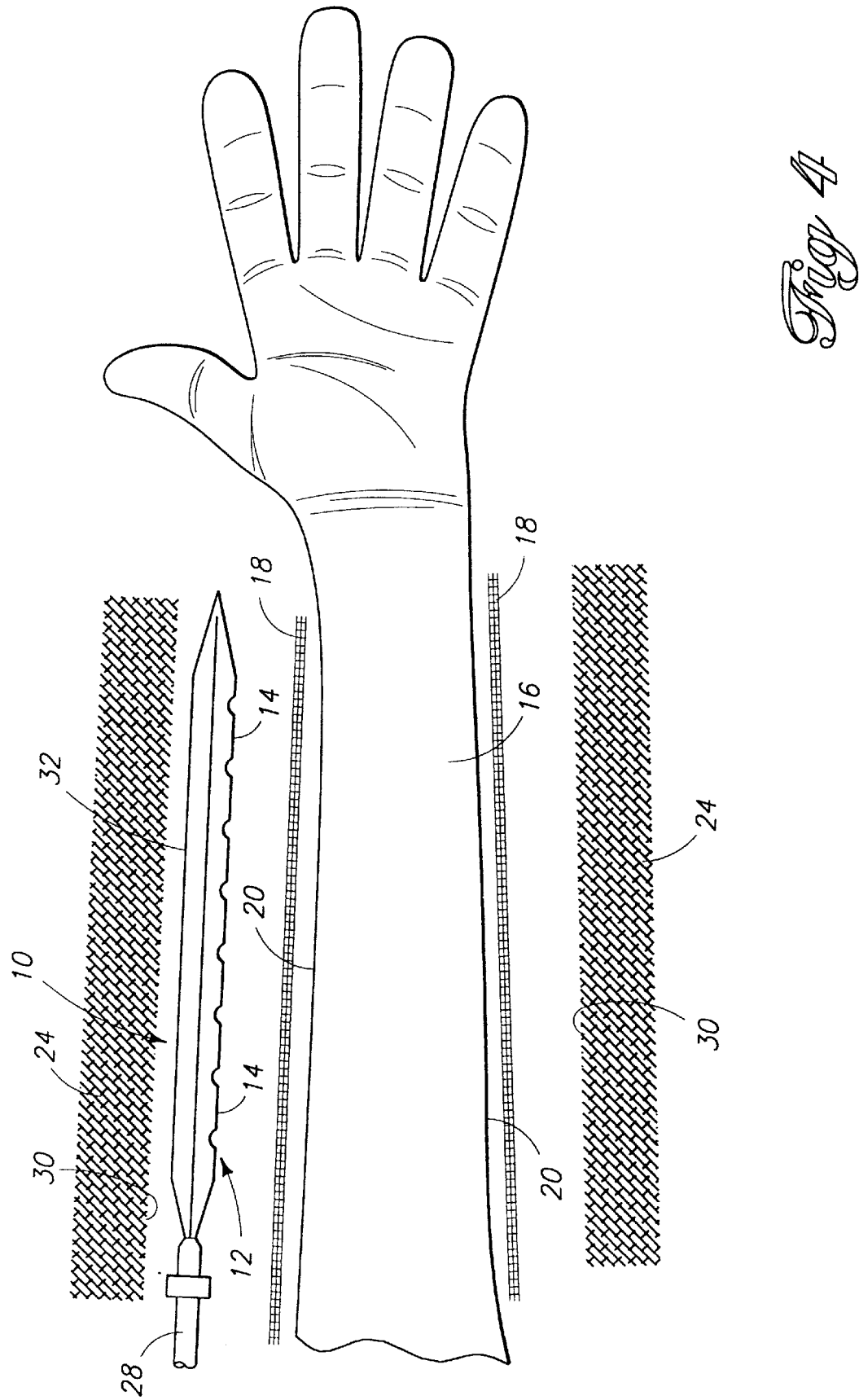

CAST VENTILATION SLEEVE

TECHNICAL FIELD

The invention relates to devices for venting orthopedic casts.

BACKGROUND INFORMATION

The use of casts for immobilizing a broken limb (broken arm, leg, etc.) is well-known. Casts are typically worn for many weeks until the broken limb heals. There is no effective way of washing the skin immediately underlying the cast and, after a period of time, bacteria build up under the cast creates skin irritation and a bad odor.

It is possible to reduce skin irritation and odor by circulating air between the cast and skin. U.S. Pat. No. 3,998,220 discloses a prior art venting device which generates a radially outward distribution of air under the cast from a disk-shaped fitting. An air coupling extending through the cast provides a means for supplying air to the fitting. Air flows from the fitting in a direction that is generally parallel to the skin surface.

Another related device is disclosed in U.S. Pat. No. 4,387,710. This patent describes a "passaged socket member" which is primarily imbedded within the cast. The socket member has a plurality of downwardly extending passageways which lead into a relatively thick "distributor layer." The distributor layer is described as being similar to the material used to make an abrasive-free cleansing pad. The distributor layer surrounds the limb and extends along the length of the cast. The socket member essentially communicates air through the wall of the cast into the distributor layer. The distributor layer creates enough of an airspace between skin and cast for air to thereafter circulate around the limb.

The present invention provides still another ventilation design having the same intended function as the devices disclosed in the above patents. However, the invention is much easier to install and much cheaper to make and use. It is also believed that it provides better circulation than the two prior devices just described. These differences, and others, will become more apparent after reviewing the following disclosure.

SUMMARY OF THE INVENTION

The invention is a device for ventilating a conventional cast. It consists of a flexible bag which rests between the inner surface of the cast and a layer of fabric, or the like, which surrounds a broken limb. At least one side of the bag, which rests directly on the fabric, has a plurality of openings arranged in one or more rows extending along the length of the bag. Since these openings are in the side of the bag which faces the limb, the openings also directly face the limb.

An orifice leading into the bag provides a connection for an air tube. Pressurized air is blown from the tube into the bag and flows out through the plurality of openings. Since the openings face the limb, they create a ventilating circulation of air directly against the outer skin along the entire length of the bag, thereby alleviating discomfort.

BRIEF DESCRIPTION OF THE DRAWINGS

In the drawings, like reference numerals refer to like parts throughout the various views, and wherein:

FIG. 2 is a top-plan view of the sleeve shown in FIG. 1;

FIG. 3 is a side-plan view of the sleeve shown in FIGS. 1-2;

FIG. 4 is an exploded view of a cast, sleeve, surrounding fabric, and limb; and

BEST MODE FOR CARRYING OUT THE INVENTION

Figure 1:
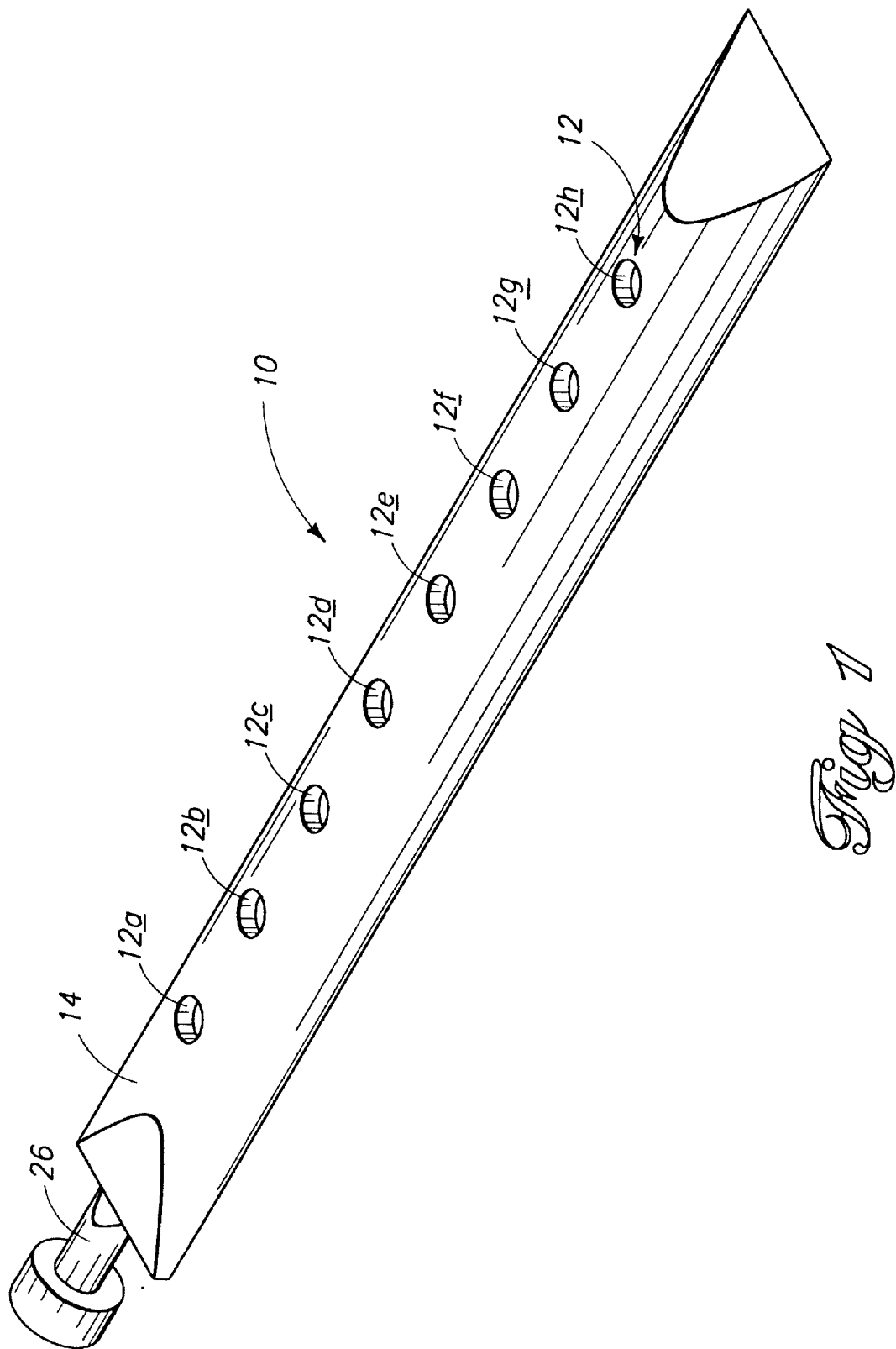
FIG. 1 is a pictorial view of a ventilation sleeve constructed in accordance with a preferred embodiment of the invention.

Referring now to FIG. 1 in the drawings, shown generally at 10 is a ventilation sleeve constructed in accordance with a preferred embodiment of the invention. The sleeve 10 is constructed from a thin, flexible polyethylene plastic material, or the like, similar to the material used to make plastic sandwich bags. FIG. 1 and the other FIGS. show the ventilation sleeve 10 in an inflated condition. When installed, as will be described later, it is in a collapsed condition such that its thickness is essentially the same as the width of the material used to make it.

While the shape of the ventilation sleeve 10 could vary, in preferred form, it has an elongated rectangular shape. A row 12 of perforations extends along and through one side 14 of the ventilation sleeve 10. The size and number of individual perforations 12a–12h may vary depending on the length and width of the sleeve 10. It is anticipated that the sleeve 10 will be made in different sizes corresponding to differences in casts or limb lengths. The specific size and shape of the ventilation sleeve 10 and number and size of the ventilation openings 12a–12h are not germane to what is considered to be the invention.

Figure 5:
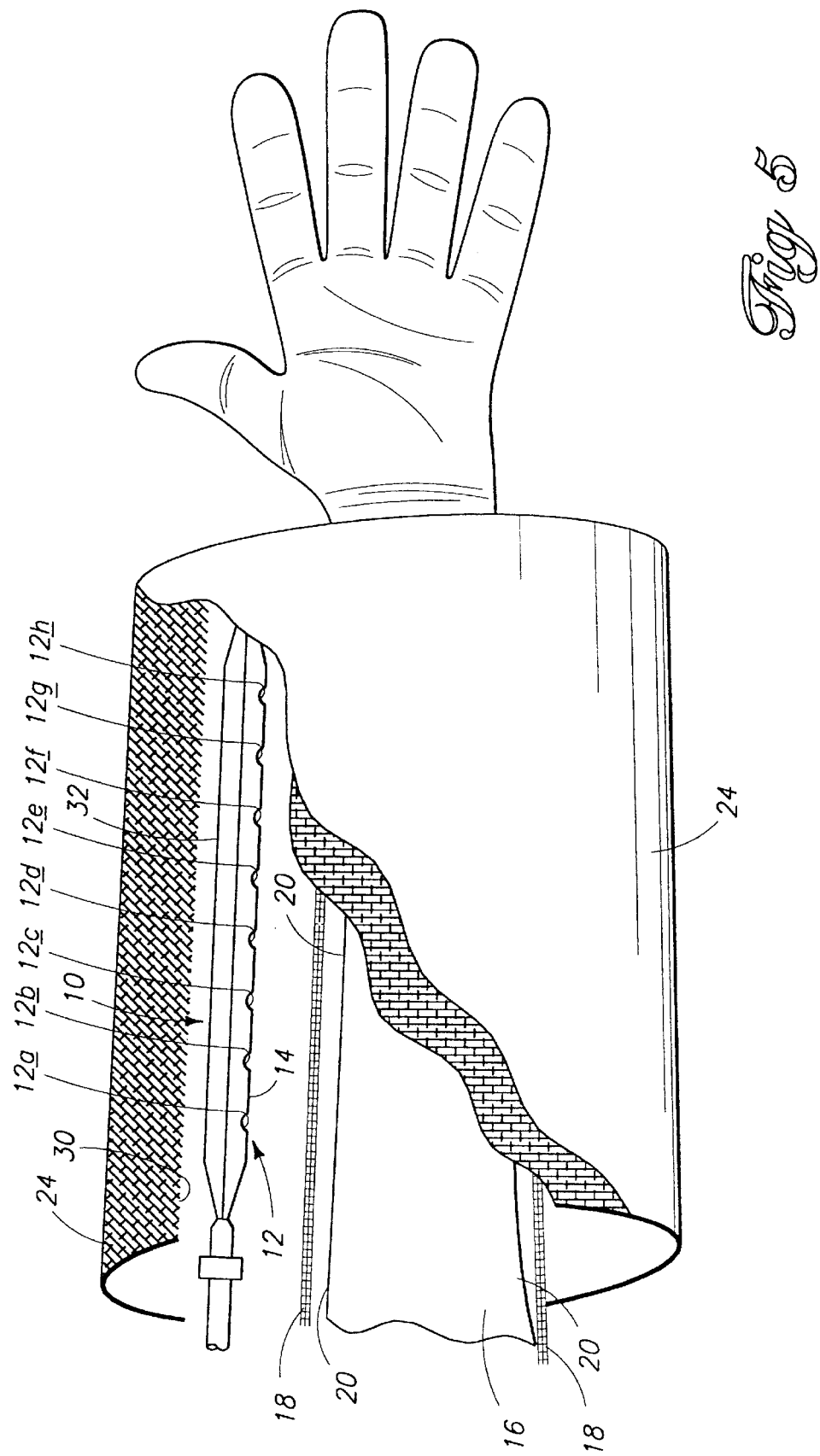
FIG. 5 is a view like FIG. 4 but shows the exterior part of the cast surrounding the limb.

Referring now to FIGS. 4 and 5, and FIG. 4 in particular, the way the ventilation sleeve 10 is used will now be described. After a broken limb such as, for example, a forearm 16 is set, it is typically surrounded with an orthopedic stockinette 18 which covers the skin 20 in the area which has been injured. The stockinette is made of cloth or another air-breathable fabric.

Normally, a cast 24 is placed around the stockinette layer 18 which completely surrounds the limb 16. Use of the present invention involves placing the ventilation sleeve 10 between the cast 24 and the stockinette layer 18 before the cast is applied. The sleeve 10 is positioned such that the perforated side 14 is the lower side as shown in FIG. 4 which faces the skin 20. This is also referred to from time to time as the "facing side." Obviously, the ventilation sleeve 10 could be placed above, below, or on each side of the limb 16. Moreover, it is conceivable that a number of ventilation sleeves could be placed within the same cast at different locations along or around the limb 16.

The ventilation sleeve 10 is collapsed when it is initially placed adjacent to the stockinette layer 18. The sleeve 10 has an air fitting 26 which is allowed to protrude from one end of the cast or, in the alternative, extends through the wall of the cast after it is set, in a fashion similar to the orifices shown in U.S. Pat. Nos. 3,998,220 and 4,387,710. The fitting 26 permits the attachment of an air tube 28 for delivering pressurized air from a compressor (not shown) to the ventilation sleeve 10.

The stockinette layer 18 provides a small amount of breathable space that enables the ventilation sleeve 10 to expand slightly as it receives air, so that the air may exit sleeve perforations 12a–12h. This is best seen in FIG. 3 and is indicated by arrows 28. As the skilled person would understand, the expansion of the sleeve 10 is exaggerated. In actuality, the space between the inner wall 30 of the cast and the outer layer of stockinette fabric 18 would not permit full air expansion of the sleeve 10.

Since the sleeve perforations 12a–12h face the skin 20, ventilation air is blown through the stockinette layer 18 directly onto the skin 20 along the length of the limb. This creates good ventilation, at least in the area where the sleeve is located. As mentioned above, cast ventilation can be enhanced by using a number of sleeves around the limb.

The preceding description sets forth the best mode for carrying out the invention as it is presently known. It is anticipated that further improvements and design variations may be made to the invention without departing from what is considered to be its scope. Consequently, the scope of patent protection is not to be limited by the preceding description. Instead, the scope of patent protection is to be limited solely by the accompanying claims, the interpretation of which is to be made in accordance with the well-established doctrines of patent claim interpretation.

What is claimed is:

1. A ventilation sleeve for ventilating a cast, the cast having a certain length and being used to immobilize a broken limb, the ventilation sleeve comprising:

an elongated flexible bag having an outer surface that faces and is positionable adjacent the limb, the outer surface having a plurality of openings which directly face the limb, the openings being arranged substantially along the length of the bag, the length of the bag so dimensioned as to be substantially equal to the length of the cast, and an orifice leading into the bag for enabling air to flow into the bag and out through the plurality of openings.

* * * * *